United States Patent [19]

Nishihira et al.

[11] Patent Number: 5,631,396

[45] Date of Patent: May 20, 1997

[54] PROCESS FOR CONTINUOUSLY PRODUCING DIMETHYL CARBONATE

[75] Inventors: Keigo Nishihira; Shinichi Yoshida; Shuji Tanaka; Yutaka Asada, all of Ube, Japan

[73] Assignee: Ube Industries, Ltd., Yamaguchi, Japan

[21] Appl. No.: 647,164

[22] Filed: May 9, 1996

[30] Foreign Application Priority Data

May 12, 1995 [JP] Japan ................... 7-114305

[51] Int. Cl.$^6$ .................................... C07C 68/00
[52] U.S. Cl. .................................... 558/277
[58] Field of Search .................................... 558/277

[56] References Cited

U.S. PATENT DOCUMENTS 5,162,563  11/1992  Nishihira et al. .
5,214,185   5/1993  Nishihira et al. .

*Primary Examiner*—Johann Richter
*Assistant Examiner*—Michael G. Ambrose
*Attorney, Agent, or Firm*—Burgess, Ryan & Wayne

[57] ABSTRACT

Dimethyl carbonate ($(CH_3O)_2CO$) is continuously produced by a catalytic reaction (first step) of CO with $CH_3NO_2$, with a significantly reduced loss of $CH_3ONO$ by the process including a second step wherein $(CH_3O)_2CO$ in a reaction product gas of the first step is absorbed by dimethyl oxalate while contacting the resultant liquid fraction with CO to recover $CH_3ONO$, a third step wherein $CH_3ONO$ is regenerated from NO in the condensed gas fraction produced in the second step and molecular oxygen and $CH_3OH$ introduced into the third step, the resultant regenerated gas fraction being recycled and reused as a feed gas for the first step, and a fourth step wherein $(CH_3O)_2CO$ contained in the liquid fraction of the second step is collected.

13 Claims, 2 Drawing Sheets

PROCESS FOR CONTINUOUSLY PRODUCING DIMETHYL CARBONATE

BACKGROUND OF THE INVENTION

2. Field of the Invention

The present invention relates to a process for continuously producing dimethyl carbonate. More particularly, the present invention relates to an industrial process for continuously producing dimethyl carbonate by a catalytic reaction in the gas phase of carbon monoxide with methyl nitrite in the presence of a solid catalyst, while collecting dimethyl carbonate by absorbing it in an absorbing medium, and effectively recovering and re-using non-reacted methyl nitrite accompanying the dimethyl carbonate absorbed in the absorbing medium.

Dimethyl carbonate is a compound useful as a material for synthesizing aromatic polycarbonates, medicines and agricultural chemicals, and as a solvent.

2. Description of the Related Art

A conventional industrial process for producing dimethyl carbonate by a catalytic reaction in the gas phase of carbon monoxide with methyl nitrite in the presence of a solid catalyst comprises, as disclosed in U.S. Pat. No. 5,214,185, a first step of catalytically reacting carbon monoxide with methyl nitrite in the gas phase in the presence of a solid catalyst in a reactor, the step of absorbing the resultant dimethyl carbonate of the first step by an absorbing medium comprising dimethyl oxalate in a dimethyl carbonate-absorbing column, the third step of bringing a non-condensed gas fraction prepared in the second step into contact with molecular oxygen and methyl alcohol in a methyl nitrite-regenerating column, to regenerate methyl nitrite from nitrogen monoxide contained in the non-condensed gas fraction, and a fourth step of distilling-collecting dimethyl carbonate from the dimethyl carbonate-containing absorbing medium in an extract-distilling column and a dimethyl carbonate-distilling column.

In the above-mentioned process, methyl nitrite is substantially not consumed in the total of the reactions as shown in the following reaction formulae:

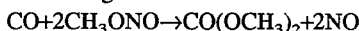
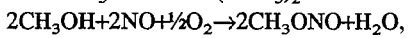

$CO+2CH_3ONO \rightarrow CO(OCH_3)_2+2NO$ $2CH_3OH+2NO+\frac{1}{2}O_2 \rightarrow 2CH_3ONO+H_2O$, and thus it appears as a substantial catalyst. However, the loss of a portion of methyl nitrite fed to the dimethyl carbonate-producing process is inevitable due to the absorption of methyl nitrite by the absorbing medium, and partial discharge of the circulating gas during the first, second and third steps. Therefore, a certain amount of methyl nitrite or nitrogen oxides must be added to the feed gas. To reduce the supplemental feed of methyl nitrite, it is important to recover non-reacted methyl nitrite with high efficiency during the process.

SUMMARY OF THE INVENTION

An object of the present invention is to provide a process for continuously producing dimethyl carbonate on an industrial scale, while effectively recovering methyl nitrite which is dissolved, together with dimethyl carbonate, in an absorbing medium in an absorbing column and could be lost.

The above-mentioned object can be attained by the process of the present invention for continuously producing dimethyl carbonate, which comprises:

a first step of introducing a feed gas containing carbon monoxide and methyl nitrite into a reactor and catalytically reacting carbon monoxide with methyl nitrite in the gas phase in the presence of a solid catalyst in the reactor, to prepare a reaction product gas comprising dimethyl carbonate mixed with a by-product containing nitrogen monoxide;

a second step of bringing the reaction product gas into contact with an absorption medium comprising dimethyl oxalate in a dimethyl carbonate-absorbing column, to provide a liquid fraction containing dimethyl carbonate absorbed by the absorbing medium and a non-condensed gas fraction containing nitrogen monoxide and non-reacted carbon monoxide and methyl nitrite;

a third step of bringing the non-condensed gas fraction of the second step into contact with molecular oxygen and methyl alcohol in a methyl nitrite-regenerating column, to regenerate methyl nitrite from the nitrogen monoxide and provide a regenerated gas fraction containing the regenerated methyl nitrite; and a fourth step of collecting dimethyl carbonate from the liquid fraction of the second step, wherein, before the fourth step, the second step liquid fraction is brought into contact with carbon monoxide, to recover methyl nitrite accompanying the second step liquid fraction and to allow the recovered methyl nitrite and the carbon monoxide to be incorporated into the non-condensed gas fraction of the second step in the absorbing column; and after the third step, at least major portion of the resultant regenerated gas fraction of the third step containing carbon monoxide and methyl nitrite is recycled as a feed gas to the reactor of the first step.

DESCRIPTION OF THE INVENTION

Figure 1:
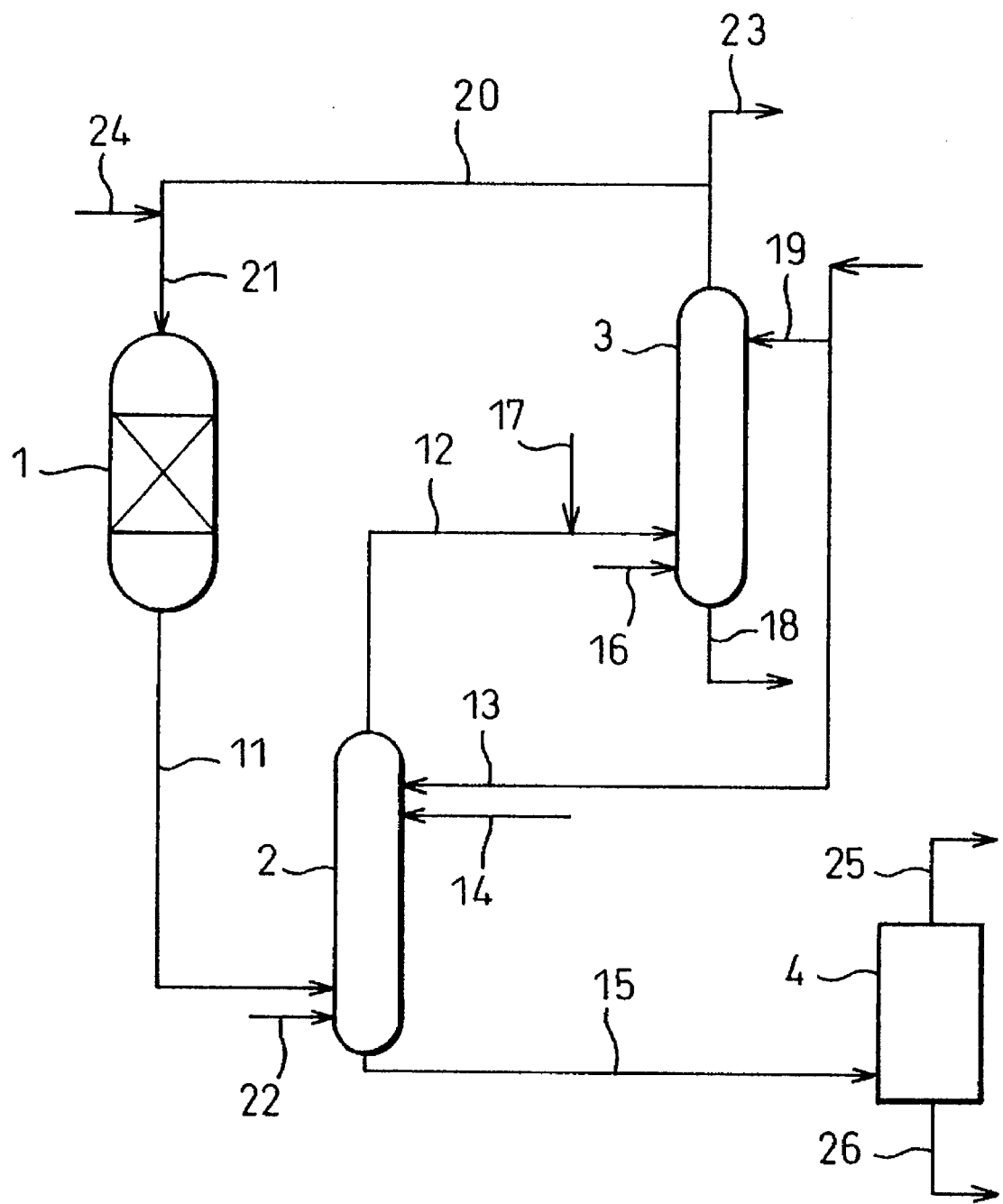
FIG. 1 is a flow sheet showing an embodiment of the process of the present invention.

The steps of the process of the present invention will be explained briefly below.

In the first step of the process of the present invention, a feed gas containing carbon monoxide and methyl nitrite is introduced into a reactor packed with a solid catalyst in which a catalytical component consisting of a platinum group metal and/or a compound thereof and optionally an assistant catalytical component carried on a carrier, to cause carbon monoxide to catalytically react with methyl nitrite in gas phase, to provide a reaction product gas containing the resultant dimethyl carbonate.

In the second step of the process of the present invention, the reaction product gas produced in the first step is introduced into a dimethyl carbonate-absorbing column (which will be referred to as an absorbing column hereinafter), and brought into contact with an absorbing medium comprising dimethyl oxalate to provide a non-condensed gas fraction containing non-reacted carbon monoxide and methyl nitrite and a by-product comprising nitrogen monoxide, and a liquid fraction separated from the non-condensed gas fraction, and comprising dimethyl carbonate absorbed by the absorbing medium.

A portion of the non-reacted methyl nitrite accompanies the liquid fraction, and the remaining portion of the non-reacted methyl nitrite accompanies the non-condensed gas fraction provided in the second step.

In the process of the present invention, before the liquid fraction prepared in the second step is introduced into the fourth step, the liquid fraction is brought into contact with carbon monoxide fed separately from the feed gas into a bottom portion of the absorbing column or between the absorbing column and the distilling column, to effectively recover methyl nitrite accompanying the liquid fraction of the second step. The recovered methyl nitrite is incorporated, together with the fed carbon monoxide, into the non-condensed gas in the absorbing column. Preferably, the contact of the liquid fraction of the second step is carried out countercurrently with carbon monoxide by bubbling a carbon monoxide gas into the liquid fraction, to enhance the recovery of methyl nitrite from the liquid fraction and to allow the recovered methyl nitrite to be incorporated together with carbon monoxide into the non-condensed gas fraction.

In the third step of the process of the present invention, the resultant non-condensed gas prepared in the absorbing column is introduced into a methyl nitrite-regenerating column (which will be referred to as a regenerating column), and brought into contact with molecular oxygen and methyl alcohol to regenerate methyl nitrite from nitrogen monoxide contained in the non-condensed gas. In the third step, a regenerated gas fraction containing carbon monoxide and methyl nitrite and a liquid reaction containing water dissolved in methyl alcohol are provided in the regenerating column.

At least a major portion of the regenerated gas fraction is recycled as a feed gas into the reactor of the first step.

In the fourth step of the process of the present invention, the liquid fraction of the second step from which the non-reacted methyl nitrite has been recovered is introduced into a dimethyl carbonate-collecting apparatus in which, preferably, methyl alcohol is collected and then dimethyl carbonate is collected from the liquid fraction.

In the process of the present invention, a closed gas-circulating system is formed through the reactor of the first step, the absorbing column of the second step and the regenerating column of the third step. The gas circulating through the closed system will be referred to us the circulating gas hereinafter. During the gas circulation, a portion of the circulating gas is discharged (purged) from the gas circulating system to control the composition and pressure of the circulating gas. Therefore, a portion of methyl nitrite contained in the circulating gas is lost. Also, a portion of methyl nitrite contained in the circulating gas is lost by being absorbed by the absorbing medium and dissolved in the liquid fraction of the third step.

The lost portion of methyl nitrite must be externally supplemented. In the process of the present invention, the portion of methyl nitrite absorbed by the absorbing medium can be recovered with a high efficiency, and thus the supplemental amount of methyl nitrite can be reduced.

The first to fourth steps of the process of the present invention will be further explained in detail below.

First Step

In the first step of the process of the present invention, dimethyl carbonate is prepared by introducing a feed gas containing carbon monoxide and methyl nitrite into a reactor packed with a solid catalyst comprising a catalytic platinum group metal element and/or compound and optionally an assistant catalytic component both carried on a carrier, so as to catalytically react carbon monoxide with methyl nitrite in the gas phase, as described in U.S. Pat. No. 5,214,185.

The solid catalyst usable for the process of the present invention may be selected from those disclosed in, for example, U.S. Pat. No. 5,162,563, comprising a catalytic component comprising at least one member selected from elements and compounds of platinum group metals and optionally, an assistant catalytic component both carried on a carrier.

The platinum group metal elements and compounds usable for the present invention may be selected from palladium, platinum, iridium, ruthenium and rhodium elements and compounds thereof. The most preferred compound is palladium chloride.

The solid catalyst may comprise an assistant catalytic component carried on the carrier and comprising at least one compound of other metals than the platinum group metals, for example, copper, iron, bismuth and cerium.

The carrier usable for the present invention comprises at least one member selected from, for example, activated carbon, alumina, silica, diatomaceous earth, zeolite and clay minerals.

A preferred solid catalyst for the process of the present invention comprises palladium chloride and cupric chloride both carried on a carrier consisting of activated carbon.

In the first step, carbon monoxide and methyl nitrite are usually diluted with an inert gas, for example, nitrogen gas or carbon dioxide gas which are inert to the catalytic reaction of the present invention, to provide a feed gas. The feed gas is fed to the reactor at a feeding rate suitable for causing the feed gas to be remained in contact with the solid catalyst preferably for a time of 10 seconds or less, more preferably 0.2 to 5 seconds. The reactor for containing the solid catalyst is preferably selected from single tube-type reactors and multiple tube type reactors.

The concentration of methyl nitrite in the feed gas is established in consideration of the reaction rate and safety thereof. Usually, in the process of the present invention, the preferable concentration of methyl nitrite in the material gas is 3 to 25% by volume.

The concentration of carbon monoxide in the feed gas is broadly variable. However, in the continuous process of the present invention, since a minor portion of the circulating gas is discharged (purged) as mentioned above, an increase in the concentration of carbon monoxide results in an increase in amount of carbon monoxide discharged to the outside of the process system, and thus is not preferred from economical point of view. Accordingly, the industrially preferable concentration of carbon monoxide in the feed gas is in the range of from 1 to 50% by volume, more preferably 5 to 30% by volume.

Usually, the catalytic reaction is carried out at a relatively low temperature, as long as the reaction rate at this temperature is satisfactory. Preferably, the reaction temperature is in the range of from 50° to 200° C., more preferably from 80° to 150° C. Also, the reaction pressure is preferably in the range of from the ambient atmospheric pressure (0 kg/cm$^2$G) to 10 kg/cm$^2$G, more preferably 1 to 6 kg/cm$^2$G.

After the catalytic reaction is completed, a reaction product gas containing dimethyl carbonate, nitrogen monoxide, carbon dioxide, non-reacted carbon monoxide and methyl nitrite and an inert gas is delivered from the reactor.

The target dimethyl carbonate is collected by introducing the reaction product gas into an absorbing column for the second step, and absorbing dimethyl carbonate by dimethyl oxalate introduced into the absorbing column through a top portion thereof.

Second Step

In the second step, dimethyl carbonate is collected from the reaction product gas by bringing the reaction product gas into contact, preferably as a counter current, with an absorbing medium consisting of dimethyl oxalate, in an absorbing column, as described in U.S. Pat. No. 5,214,185.

The countercurrent contact may be carried out in any type of absorbing column. Preferably, the absorbing column is selected from packed columns and plate columns.

In the absorbing column, the feeding rate of dimethyl oxalate is variable depending on the amount of dimethyl carbonate contained in the reaction product gas and introduced into the absorbing column. Usually, dimethyl oxalate is preferably fed in an amount of 3 to 10 times, more preferably 4 to 6 times the weight of dimethyl carbonate fed into the absorbing column.

To effect the absorption of dimethyl carbonate with a high efficiency, the absorbing temperature is preferably low. However, if the absorbing temperature is too low, dimethyl oxalate is solidified and the necessary energy consumption for the absorption disadvantageously increases. Therefore, the absorption is carried out preferably at a temperature of 0° to 100° C., more preferably 30° to 80° C.

In the second step, an absorbing medium liquid fraction comprising dimethyl carbonate absorbed by dimethyl oxalate and a non-condensed gas fraction containing nitrogen monoxide are provided. The liquid fraction also contains a portion of the non-reacted methyl nitrite.

In the process of the present invention, before the liquid fraction prepared in the second step is introduced into the dimethyl carbonate collecting apparatus of the fourth step, carbon monoxide, fed separately from the feed gas, is brought into contact with the liquid fraction of the second step, to effectively recover methyl nitrite accompanying the liquid fraction and allow the recovered methyl nitrite to be incorporated together with the fed carbon monoxide into the non-condensed gas fraction in the absorbing column. The incorporated non-condensed gas fraction is introduced into the regenerating column of the third step. The recovery of methyl nitrite from the liquid fraction of the second and the incorporation of the recovered methyl nitrite into the non-condensed gas fraction effectively decreases the loss of methyl nitrite occurring between the second step and the third step and causes the amount of methyl nitrite or nitrogen oxides to be added to the third step.

Also, the recovery of methyl nitrite effectively causes the partially discharged (purged) amount of the circulating gas and the supplementary amount of carbon monoxide to decrease. Further, since the recovered methyl nitrite is recycled to the first step and reused to prepare dimethyl carbonate, carbon monoxide can be effectively supplemented in response to the consumption of carbon monoxide during the dimethyl carbonate-producing reaction in the first step and the decrease in carbon monoxide amount due to the partial discharge (purge) of the circulating gas.

There is no limitation to the method of bringing carbon monoxide fed from the outside of the gas circulating system and thus separately from the feed gas into contact countercurrently with the liquid fraction of the second step. In an embodiment, carbon monoxide is introduced into a bottom portion of the absorbing column through an inlet located below the inlet for the reaction product gas fed from the reactor of the first step, flows upward through the bottom portion of the absorbing column, and is brought into contact countercurrently with the liquid fraction formed in the absorbing column and flowing downward therethrough. Alternatively, a gas-liquid contact apparatus is arranged between the absorbing column of the second step and the distilling column of the fourth step, carbon monoxide is introduced into a bottom portion of the gas-liquid contact apparatus so as to flow upward through the gas-liquid contact apparatus and then toward the regenerating column, the liquid fraction of the second step is introduced into a top portion of the gas-liquid contact apparatus so as to flow downward through the gas-liquid contact column and then toward the dimethyl carbonate-collecting apparatus of the fourth step, and thus carbon monoxide flow and the liquid fraction flow are brought into contact counter currently with each other. There is no limitation to the type of the gas-liquid contact apparatus as long as the apparatus allows full contact of the liquid fraction with carbon monoxide and fully releases methyl nitrite from the liquid fraction. Preferably, the gas-liquid contact apparatus is selected from packed columns and plate columns.

The carbon monoxide to be fed from the outside of the circulating system for the purpose of recovery of methyl nitrite from the liquid fraction may be pure carbon monoxide or carbon monoxide diluted with an inert gas, for example, nitrogen. However, to avoid an undesirably large increase in the total amount of the circulating gas, and to decrease the discharging (purging) amount of the circulating gas, pure carbon monoxide is preferably used for the recovery of methyl nitrite.

The amount of carbon monoxide to be brought into contact with the liquid fraction of the second step is in the range of from the amount corresponding to the loss of the carbon monoxide content in the circulating gas due to the partial discharge (purge) of the circulating gas to the amount corresponding to the total content of carbon monoxide in the feed gas. The above-mentioned loss of carbon monoxide corresponds to 5 to 50% by volume of the total amount of carbon monoxide in the feed gas.

The amount of carbon monoxide to be fed for the purpose of recovering methyl nitrite from the liquid fraction of the second step can be selected in the above-mentioned range in response to necessity. For example, where carbon monoxide is fed in an amount corresponding to the loss of carbon monoxide due to the reaction thereof in the first step and the partial discharge (purge) of the circulating gas, the supplementary amount of carbon monoxide preferably corresponds to 5 to 50% by volume of the total content of carbon monoxide in the feed gas.

When carbon monoxide must be contained in an excessive amount in the feed gas, carbon monoxide may be fed in an amount corresponding to 5 to 50% by volume of the total content of carbon monoxide in the feed gas into contact with the liquid fraction of the second step, and the remaining amount of carbon monoxide may be mixed in the gas fraction delivered from the regenerating column of the third step. Also, in the process of the present invention, all or a portion of carbon monoxide contained in the feed gas to be fed into the reactor of the first step can be supplied by bringing carbon monoxide into contact with the liquid fraction of the second step, to recover methyl nitrite.

After the contact of the liquid fraction with carbon monoxide, the resultant liquid fraction, from which methyl nitrite is recovered, is fed to the dimethyl carbonate-collecting apparatus of the fourth step.

The recovered methyl nitrite from the liquid fraction of the second step is incorporated, together with the fed carbon monoxide, into the non-condensed gas fraction, residing in the absorbing column or delivered from the top of the absorbing column, and the resultant incorporated non-condensed gas fraction is introduced into the regenerating column of the third step.

The incorporated non-condensed gas fraction contains dimethyl carbonate and a small amount of dimethyl oxalate. If the incorporated non-condensed gas fraction is subjected to the regenerating reaction, the dimethyl carbonate and the small amount of dimethyl oxalate become a loss. To avoid the loss, preferably a small amount of methyl alcohol is fed into the absorbing column through an inlet located above the inlet for dimethyl oxalate in the top portion of the absorbing column, to remove dimethyl carbonate and dimethyl oxalate from the incorporated non-condensed gas fraction by methyl alcohol. Methyl alcohol is fed preferably in an amount of 5 to 50% by weight, more preferably 10 to 20% by weight, based on the weight of dimethyl carbonate contained in the reaction product gas.

The incorporated non-condensed gas fraction delivered from the absorbing column of the second step contains, in addition to the non-reacted carbon monoxide and methyl nitrite, a large amount of nitrogen monoxide produced in the first step, and thus in the next third step, nitrogen monoxide is regenerated into methyl nitrite in the regenerating column.

Third Step

In the third step of the process of the present invention, methyl nitrite is regenerated by introducing the incorporated non-condensed gas into the regenerating column and bringing it into contact with a molecular oxygen-containing gas and methyl alcohol, by the method as described in, for example, U.S. Pat. No. 5,214,185. The contact of the incorporated non-condensed gas with methyl alcohol and molecular oxygen is carried out preferably at a temperature of 60° C. or less, more preferably 0° to 50° C., for a contact time of 0.5 to 2 seconds.

The regenerating column is selected from packing columns, bubbling columns, spraying columns and tray columns which are all conventionally employed as a gas-liquid contact reaction apparatus.

The molecular oxygen-containing gas usable for the process of the present invention may be a pure oxygen gas, a mixed gas consisting of oxygen diluted with an inert gas, for example, nitrogen gas, or air.

In the third step, the molecular oxygen-containing gas is fed in an amount of 0.08 to 0.2 mole in terms of oxygen per mole of nitrogen monoxide introduced into the regenerating column.

In the third step, methyl alcohol is fed in a necessary amount or more to completely absorb and react with nitrogen dioxide produced from nitrogen monoxide and the molecular oxygen and with nitrogen monoxide in an amount substantially equal to the molar amount of the nitrogen dioxide.

The amount of methyl alcohol fed into the regenerating column is usually 2 to 5 moles per mole of nitrogen monoxide contained in the incorporated non-condensed gas introduced in the regenerating column. Further, to compensate the loss of methyl nitrite, methyl nitrite or nitrogen oxides (including nitrogen monoxide, nitrogen dioxide, dinitrogen trioxide and dinitrogen tetraoxide) in a supplementary amount may be mixed with the incorporated non-condensed gas and the molecular oxygen, and the mixed gas may be fed to the regenerating column of the third step.

A liquid fraction delivered from the regenerating column of the third step comprises a methyl alcohol solution of water produced by the regenerating reaction for methyl nitrite. Therefore, methyl alcohol is collected from the liquid fraction of the third step by, for example, distillation and reused in the second and third step. Also, the regenerated gas fraction delivered from the regenerating column contains methyl nitrite and carbon monoxide and is recycled as a feed gas into the reactor of the first step through the gas circulating system, to reuse it for the production of dimethyl carbonate.

Fourth Step

After recovering methyl nitrite from the liquid fraction of the second step, the remaining liquid fraction which contains dimethyl carbonate absorbed by dimethyl oxalate is introduced into the dimethyl carbonate-collecting apparatus of the fourth step. In the fourth step, dimethyl carbonate is collected from the liquid fraction by distillation, preferably after methyl alcohol and a small amount of a by-product consisting of compounds having a low boiling temperature, such as methyl formate are removed from the liquid fraction by an extract-distillation with dimethyl oxalate, in accordance with the method described, for example, in U.S. Pat. No. 5,214,185, and then dimethyl carbonate is collected by distillation.

The process of the present invention will be further explained particularly by referring to FIGS. 1 and 2 below.

Figure 2:
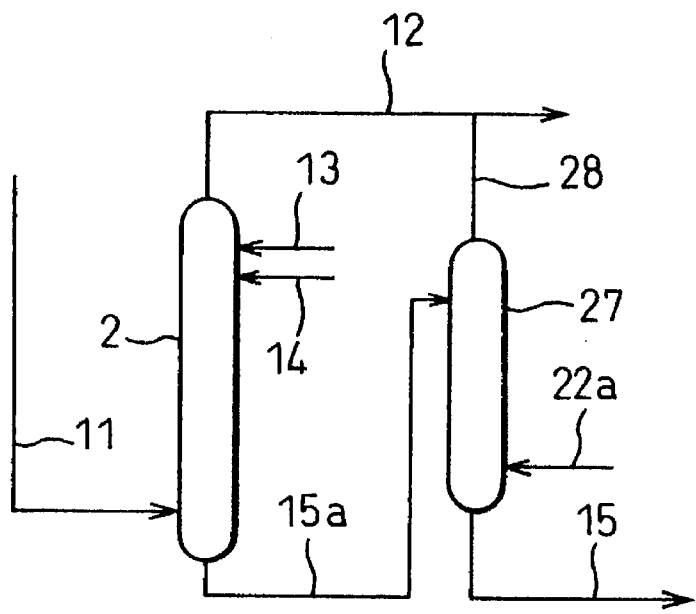
FIG. 2 is a flow sheet showing a portion of another embodiment of the process of the present invention.

Referring to FIG. 1 showing an embodiment of the process of the present invention, a feed gas containing carbon monoxide, methyl nitrite and nitrogen monoxide is introduced into a top portion of a reactor 1, for example, a multiple tube type reactor, having reaction tubes packed with a platinum group metal-containing solid catalyst through conduits 20 and 21, optionally after the feed gas is pressurized by a gas-circulator (not shown in FIG. 1) arranged in the conduit 20. In the reactor, a catalytical reaction of carbon monoxide with methyl nitrite in gas phase is carried out while contacting the feed gas with the solid catalyst, and the resultant reaction product gas passed through the catalyst layer is delivered from a bottom portion of the reactor 1 and is introduced into a bottom portion of an absorbing column 2 through a conduit 11. Into a top portion of the absorbing column 2, methyl alcohol is introduced through a conduit 13 and dimethyl oxalate is introduced through a conduit 14. The introduced reaction product gas is brought into contact countercurrently with the introduced methyl alcohol and dimethyl oxalate, to cause dimethyl carbonate in the reaction product gas to be absorbed by dimethyl oxalate. As a result, a liquid fraction containing dimethyl carbonate absorbed by dimethyl carbonate and methyl alcohol and a non-condensed gas fraction containing nitrogen monoxide and non-reacted carbon monoxide are provided in the absorbing column 2. The non-reacted methyl nitrite contained in the reaction product gas is distributed in both the liquid fraction and the non-condensed gas fraction.

A supplementary amount of carbon monoxide is fed into the bottom portion of the absorbing column 2 through a conduit 22 connected to the absorbing column 2 at a location below the location at which the conduit 11 for the reaction product gas is connected to the absorbing column 2. The fed carbon monoxide is brought into counter current contact with the liquid fraction to cause methyl nitrite contained in the liquid fraction to be recovered from the liquid fraction and to be incorporated, together with the fed carbon monoxide, into the condensed gas fraction. The methyl nitrite-removed liquid fraction is delivered from the bottom portion of the absorbing column 2 and is forwarded to a distilling column 4 for the fourth step through a conduit 15. In the fourth step, dimethyl carbonate is collected from the liquid fraction delivered from the second step by distillation. The distilled dimethyl carbonate is collected from the distilling column 4 through conduit 25 and a distillation residue is discharged from the distilling column 4 through a conduit 26.

The non-condensed gas incorporated with carbon monoxide and the recovered methyl nitrite is delivered from the top portion of the absorbing column 2 and is introduced into a bottom portion of a regenerating column 3 for the third step through a conduit 12.

When the incorporated non-condensed gas delivered from the absorbing column 2 contains a nitrogen supply source in a content insufficient to regenerate methyl nitrite in a desired amount in the regenerating column 3, a supplementary amount of methyl nitrite or nitrogen oxides is fed into the conduit 12 through a conduit 17 and is mixed into the incorporated non-condensed gas fraction.

In the regenerating column 3, a molecular oxygen-containing gas is introduced into the bottom portion of the regenerating column 3 through a conduit 16 which is connected to the regenerating column 3 at a location below the location at which the conduit 12 is connected to the regenerating column, and mixed with the incorporated non-condensed gas fraction. The mixed gas is brought into contact countercurrently with methyl alcohol introduced into a top portion of the regenerating column 3 through a conduit 19, to regenerate methyl nitrite from nitrogen monoxide. As a result, a regenerated gas fraction containing methyl nitrite, carbon monoxide and a liquid fraction containing water which is a by-product of the methyl nitrite-regenerating reaction and is dissolved in methyl alcohol are provided in the regenerating column 3. The regenerated gas fraction is delivered from the top portion of the regenerating column 3 through a conduit 20. At least a major portion of the regenerated gas fraction delivered through the conduit 20 is recycled as a feed gas into the reactor 1 of the first step through a conduit 21. As shown in FIG. 1, a supplementary amount of carbon monoxide is optionally introduced into the conduit 20 through a conduit 24 and mixed into the feed gas.

Optionally, a portion of the regenerated gas fraction delivered from the regenerating column is discharged (purged) through a conduit 23 to the outside of the gas circulating system.

The liquid fraction containing water dissolved in methyl alcohol is delivered from the bottom portion of the regenerating column 3 through a conduit 18. The delivered liquid fraction is subjected to water removal by distillation or another water-removing method, to refine methyl alcohol. The refined methyl alcohol is recycled to the absorbing column 2 of the second step through the conduit 13 and to the regenerating column 3 of the third step through the conduit 19.

In another embodiment of the process of the present invention, the contacting of the liquid fraction of the second step with carbon monoxide is effected outside of the absorbing column 2. Referring to FIG. 2, a gas-liquid contact apparatus 27 is arranged downstream from the bottom of the absorbing column 2. The liquid fraction delivered from the bottom of the absorbing column 2 is introduced into a top portion of the gas-liquid contact apparatus 27 through a conduit 15a, and a supplementary amount of carbon monoxide is introduced into a bottom portion of the gas-liquid contact apparatus 27 through a conduit 22a. The introduced liquid fraction and carbon monoxide are brought into contact countercurrently with each other, to recover methyl nitrite from the liquid fraction. The recovered methyl nitrite mixed with carbon monoxide is delivered from the top of the gas-liquid contact apparatus 27 and is introduced into the conduit 12 through a conduit 28 and is then incorporated into the non-condensed gas fraction delivered from the absorbing column 2B. Also, the methyl nitrite-removed liquid fraction is delivered from the bottom of the gas-liquid contact apparatus 27 through the conduit 15 and introduced into the dimethyl carbonate-collecting apparatus (not shown in FIG. 2) of the fourth step.

Figure 3:
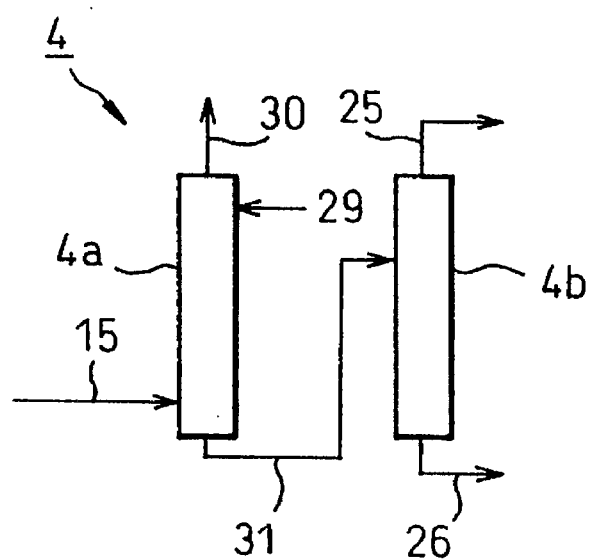
FIG. 3 is a flow sheet showing a preferable embodiment of the fourth step of the process of the present invention.

Referring to FIG. 3 showing an preferable embodiment of the fourth step of the process of the present invention, a dimethyl carbonate-collecting apparatus 4 is provided with an extract-distilling column 4a and a distilling column 4b.

The liquid fraction of the second step from which methyl nitrite has been recovered is introduced into a bottom portion of the extract-distilling column 4a through the conduit 15, and dimethyl oxalate is introduced into a top portion of the extract-distilling column 4a through a conduit 29. In this extract-distilling column 4b, methyl alcohol is collected and recovered from the introduced liquid fraction, and the recovered methyl alcohol is delivered from the top of the extract-distilling column 4a through a conduit 30. The resultant liquid fraction of the extract distilling column 4a is introduced into the distilling column 4b through a conduit 31 and dimethyl carbonate is distilled in this distilling column 4b and collected through a conduit 25. Also, the resultant distillation residue is discharged from the distilling column 4b through a conduit 26.

EXAMPLES

The present invention will be further explained by the following specific examples, in comparison with the comparative examples.

In the examples, the space time yield (STY) in kg/m³·hr of dimethyl carbonate was calculated in accordance with the following equation (I):

$$STY \ (kg/m^3 \cdot hr) = a/(b \times \theta) \qquad (I)$$

wherein $\theta$ represents a catalytic reaction time in hours of carbon monoxide with methyl nitrite in a reaction tube, a represents a weight in kg of the resultant dimethyl carbonate during the catalytic reaction time $\theta$, and b represents a volume in m³ of a solid catalyst packed in the reaction tube.

EXAMPLE 1

Preparation of Dimethyl Carbonate

A multiple tube type reactor made from a stainless steel and equipped with 20 reaction tubes each having an inside diameter of 27 mm and a length (height) of 3 m was packed with 34.0 liters of a solid catalyst as disclosed in U.S. Pat. No. 5,162,563, in the form of pellets each having a diameter of 4 mm and a length of 6 mm and comprising palladium chloride and cupric chloride carried on a carrier consisting of activated carbon available under the Trademark of Shirasagi from Takeda Yakuhin K.K. Catalyst layers were formed in the reaction tubes. The reactor was further equipped with a jacket surrounding a shell of the reactor, through which jacket a heating medium flows.

A feed gas comprising 20.0% by volume of carbon monoxide, 15.0% by volume of methyl nitrite, 4.0% by volume of nitrogen monoxide, 7.0% by volume of methyl alcohol, 2.0% by volume of carbon dioxide, and 52.0% by volume of nitrogen was pressurized by a gas compressor to a pressure of 4.02 kg/cm$^2$G, pre-heated to a temperature of about 90° C. in a heat exchanger, and then fed into a top portion of the reactor at a feeding rate of 136 Nm$^3$/hr under the above-mentioned pressure while maintaining the temperature of the center portions of the catalyst layers at a level of about 125° C. by circulating hot water through the jacket, to cause carbon monoxide to catalytically react with methyl nitrite.

In this reaction, the space time yield (STY) of dimethyl carbonate was 342 kg/m$^3$·hr.

The resultant reaction product gas passed through the catalyst layers was withdrawn from the reactor and introduced into a bottom portion of an absorbing column consisting of a Pole ring packing type gas-liquid contact absorbing apparatus (absorbing column) having an inside diameter of 300 mm and a length (height) of 5 m, through an inlet located 1500 mm above the bottom of the column. Simultaneously, carbon monoxide was introduced at a feeding rate of 3.6 Nm$^3$/hr, into the bottom portion of the absorbing column through an inlet located 1000 mm above the bottom of the column, methyl alcohol was introduced at a feeding rate of 3.6 liters/hr into the top of the absorbing column and dimethyl oxalate was introduced at a feeding rate of 50.0 kg/hr into a middle portion of the absorbing column through an inlet located 1000 mm below the top of the column, so that the reaction product gas was brought into contact countercurrently with the introduced methyl alcohol and dimethyl oxalate at a column top temperature of 35° C. and at a column bottom temperature of 55° C. As a result, a liquid fraction was obtained in an amount of 65.7 kg/hr from the bottom of the absorbing column. The liquid fraction comprised 77.7% by weight of dimethyl oxalate, 17.3% by weight of dimethyl carbonate, 4.2% by weight of methyl alcohol, 0.1% by weight of methyl formate and 0.1% by weight of methyl nitrite.

Also, a non-condensed gas fraction was withdrawn at a flow rate of 136.4 Nm$^3$/hr from the top portion of the absorbing column. The withdrawn non-condensed gas contained 20.2% by volume of carbon monoxide, 10.5% by volume of methyl nitrite, 8.4% by weight of nitrogen monoxide, 2.1% by volume of carbon dioxide, 7.0% by volume of methyl alcohol and 51.8% by volume of nitrogen. The withdrawn non-condensed gas contained methyl nitrite in a lower concentration than that in the feed gas. Therefore, the non-condensed gas was introduced into a regenerating column of a third step to regenerate methyl nitrite.

The non-condensed gas was mixed in an amount of 136.4 Nm$^3$/hr with 1.63 Nm$^3$/hr of oxygen gas and 1.5 Nm$^3$/hr of nitrogen gas containing 30.0% by volume of nitrogen monoxide, and the resultant mixed gas was introduced into the regenerating column consisting of a gas-liquid contact-absorbing apparatus (regenerating column) having an inside diameter of 300 mm and a length (height) of 6.4 m. The introduced mixed gas was brought into contact countercurrently with methyl alcohol introduced at a flow rate of 20 liter/hr into the top portion of the regenerating column, at a column top temperature of 30° C. and at a column bottom temperature of 40° C., to regenerate methyl nitrite.

The resultant regenerated gas fraction was delivered in an amount of 138.0 Nm$^3$/hr from the top of the regenerated column, and a minor portion of the regenerated gas fraction was discharged in an amount of 2.0 Nm$^3$/hr to remove the inert gas from the regenerated gas fraction. Thereafter, the remaining major portion of the regenerated gas faction is pressurized by a gas compressor, and then introduced, as a feed gas containing 20.0% by volume of carbon monoxide, 15.0% by volume of methyl nitrite, 4.0% by volume of nitrogen monoxide, 7.0% by volume of methyl alcohol, 1.0% by volume of carbon dioxide and 52.0% by volume of nitrogen, into the reaction.

Also, a liquid fraction in an amount of 9.2 kg/hr of methyl alcohol containing 28.0% by weight was delivered from the bottom of regenerating column. The liquid fraction was subjected to removal of water by distillation. The resultant refined methyl alcohol was distributed to the absorbing column of the second step and the regenerating column of the third step and reused therein.

The methyl nitrite-recovered liquid fraction delivered in an amount of 65.7 kg/hr from the bottom of the absorbing column of the second step was subjected to dimethyl carbonate-collecting procedures of the fourth step and the resultant refined dimethyl carbonate was continuously collected in an amount of 11.2 kg/hr.

COMPARATIVE EXAMPLE 1

The same procedures as in Example 1 were carried out with the following exceptions.

In the first step, a feed gas comprising 20.0% by volume of carbon monoxide, 15.0% by volume of methyl nitrite, 4.0% by volume of nitrogen monoxide, 7.0% by volume of methyl alcohol, 1.0% by volume of carbon dioxide, and 53.0% by volume of nitrogen, was fed into the reaction.

In this first step, the space time yield (STY) of dimethyl carbonate was 342 kg/m$^3$·hr.

In the second step, no carbon monoxide was fed into the absorbing column, and thus the recovery of methyl nitrite from the liquid fraction of the second step was not effected.

In the second step, the same absorbing procedures of dimethyl carbonate contained in the reaction product gas by dimethyl oxalate as in Example 1 are carried out. The liquid fraction delivered from the bottom of the absorbing column was in an amount of 66.0 kg/hr and contained 0.5% by weight of methyl nitrite.

The third and fourth steps were carried out in the same manner as in Example 1.

The non-condensed gas was delivered in an amount of 132.8 Nm$^2$/hr from the top of the absorbing column was mixed with 1.74 Nm$^3$/hr of a molecular oxygen gas and 3.6 Nm$^3$/hr of a nitrogen gas containing 30.0% by volume of nitrogen monoxide. The resultant mixed gas was introduced into the bottom portion of the regenerating column of the third step and brought into contact countercurrently with methyl alcohol introduced in an amount of 21 liter/hr of methyl alcohol into the top portion of the regenerating column, at a column top temperature of 30° C. and at a column bottom temperature of 40° C., to regenerate methyl nitrite.

The resultant regenerated gas fraction delivered from the top of the regenerating column was in an amount of 136.6 Nm$^3$/hr and comprised 17.6% by volume of carbon monoxide, 15.5% by volume of methyl nitrite, 4.1% by volume of nitrogen monoxide, 7.2% by volume of methyl alcohol, 1.1% by volume of carbon dioxide, and 54.4% by volume of nitrogen. After a minor portion of the delivered regenerated gas fraction was discharged in an amount of 4.6 Nm$^3$/hr, a remaining major portion of the delivered regenerated gas fraction was pressurized by a gas compressor and mixed with 4.0 Nm$^3$/hr of carbon monoxide fed through a conduit 24. The resultant mixed gas comprising 20.0% by volume of carbon monoxide, 15.0% by volume of methyl nitrite, 4.0% by volume of nitrogen monoxide, 7.0% by volume of methyl alcohol, 1.0% by volume of carbon dioxide and 53.0% by volume of nitrogen was introduced as a feed gas into the reactor of the first step.

The liquid fraction delivered from the regenerating column of the third step comprised 9.3 kg/hr of methyl alcohol containing 29.0% by weight of water. The liquid fraction was refined by removing water by distillation. The resultant refined methyl alcohol was reused in the absorbing column of the second step and the regenerating column of the third step.

The liquid fraction delivered in an amount of 66.0 kg/hr from the bottom of the absorbing column of the second step was distilled in the fourth step. Dimethyl carbonate was continuously collected in an amount of 11.2 kg/hr.

The lost amounts of methyl nitrite and supplemented amounts of nitrogen amounts and the others in Example 1 and Comparative Example 1 are shown in Table 1.

TABLE 1

|  |  | Example 1 | Comparative Example 1 |
|---|---|---|---|
| Loss of methyl nitrite (kg/hr) | | 0.066 | 0.330 |
| Supplement | Nitrogen oxides (Nm³/hr) | 1.5 | 3.6 |
| | Oxygen (Nm³/hr) | 1.63 | 1.74 |
| | Methyl alcohol (liter/hr) | 20 | 21 |
| | Carbon monoxide (Nm³/hr) | 3.6 | 4.0 |
| Discharged amount of circulating gas (Nm³/hr) | | 2.0 | 4.6 |

Note: Loss of methyl nitrite (kg/hr) = (Amount (kg/hr) of second step liquid fraction) × (concentration of methyl nitrite in second step liquid fraction)

Table 1 clearly shows that in the process of Example 1 in accordance with the present invention, the loss of methyl nitrite is significantly small, and thus the addition of nitrogen oxides is very small. In Comparative Example 1 wherein no recovery of methyl nitrite from the liquid fraction of the second step was carried out, the loss of methyl nitrite was large and thus the addition of a large amount of nitrogen oxides was necessary.

Also, in Example 1, the amount of the discharged circulating gas is significantly smaller than that of Comparative Example 1.

In the process of the present invention for continuously producing dimethyl carbonate by an industrial reaction procedure of carbon monoxide with methyl nitrite in the presence of solid catalyst, a portion of non-reacted methyl nitrite contained in the liquid fraction formed in the absorbing column of the second step, which will be lost, can be effectively recovered. Therefore, in the process of the present invention, the loss of methyl nitrite can be significantly reduced, and thus amount of nitrogen oxides or methyl nitrite necessary to supplement to the third step can be significantly decreased, and the discharged amount of the circulating gas from the circulating system can be reduced. Also, the process of the present invention can reduce the amount of carbon monoxide to be supplemented to the circulating gas.

Accordingly, the process of the present invention is advantageous in the industrial continuous production of dimethyl carbonate with a significantly enhanced utilization efficiency of methyl nitrite and carbon monoxide.

What we claim is:

1. A process for continuously producing dimethyl carbonate comprising:

a first step of introducing a feed gas containing carbon monoxide and methyl nitrite into a reactor and catalytically reacting carbon monoxide with methyl nitrite in a gas phase in the presence of a solid catalyst in the reactor, to prepare a reaction product gas comprising dimethyl carbonate mixed with a by-product containing nitrogen monoxide;

a second step of bringing the reaction gas into contact with an absorption medium comprising dimethyl oxalate in a dimethyl carbonate-absorbing column, to provide a liquid fraction containing dimethyl carbonate absorbed by the absorbing medium and a non-condensed gas fraction containing nitrogen monoxide and non-reacted carbon monoxide and methyl nitrite;

a third step of bringing the non-condensed gas fraction of the second step into contact with molecular oxygen and methyl alcohol in a methyl nitrite-regenerating column, to regenerate methyl nitrite from the nitrogen monoxide and provide a regenerated gas fraction containing the regenerated methyl nitrite; and a fourth step of collecting dimethyl carbonate from the liquid fraction of the second step, wherein before the fourth step, the second step liquid fraction is brought into contact with carbon monoxide, to recover methyl nitrite accompanying with the second step liquid fraction and allow the recovered methyl nitrite and the carbon monoxide to be incorporated into the non-condensed gas fraction of the second step in the absorbing column; and after the third step, at least a major portion of the resultant regenerated gas fraction of the third step containing carbon monoxide and methyl nitrite is recycled as a feed gas to the reactor of the first step.

2. The process as claimed in claim 1, wherein the solid catalyst comprises palladium chloride and cupric chloride carried on a carrier consisting of activated carbon.

3. The process as claimed in claim 1, wherein the feed gas of the first step comprises carbon monoxide in a concentration of 1 to 50% by volume and methyl nitrite in a concentration of 1 to 25% by volume.

4. The process as claimed in claim 1, wherein, in the first step, the catalytic reaction is carried out at a temperature of 50° to 200° C. under a pressure of from 0 to 10 kg/cm²G.

5. The process as claimed in claim 1, wherein, in the second step, dimethyl oxalate is used in an amount of 3 to 10 times the weight of dimethyl carbonate introduced into the second step, and the reaction product gas of the first step is brought into contact countercurrently with the absorbing medium.

6. The process as claimed in claim 1, wherein, the second step is carried out at a temperature of 0° to 100° C.

7. The process as claimed in claim 1, wherein, before the fourth step, the second step liquid fraction is brought into contact countercurrently with carbon monoxide.

8. The process as claimed in claim 1, wherein, before the fourth step, the contacting of the second step liquid fraction with carbon monoxide is carried out in a bottom portion of the absorbing column.

9. The process as claimed in claim 1, wherein, before the fourth step, the contacting of the second step liquid fraction with carbon monoxide is carried out in a gas-liquid contact apparatus located downstream from the bottom of the absorbing column of the second step.

10. The process as claimed in claim 1, wherein, in the second step, methyl alcohol is introduced into the dimethyl carbonate-absorbing column to recover dimethyl carbonate and dimethyl oxalate accompanying with the non-condensed gas, and the introduced methyl alcohol is in an amount of 5 to 30% by weight based on the weight of dimethyl carbonate introduced into the dimethyl carbonate-absorbing column.

11. The process as claimed in claim 1, wherein, in the third step, the molecular oxygen is present in an amount of 0.08 to 0.2 mole per mole of nitrogen monoxide introduced into the methyl nitrite-regenerating column.

12. The process as claimed in claim 1, wherein, in the third step, the contacting of the non-condensed gas with the molecular oxygen and methyl alcohol is carried out at a temperature of 60° C. or less.

13. The process as claimed in claim 1, wherein, in the third step, the introduced methyl alcohol is in an amount of 2 to 5 moles per mole of nitrogen monoxide introduced into the methyl nitrite-regenerating column.

* * * * *